Figure 1:
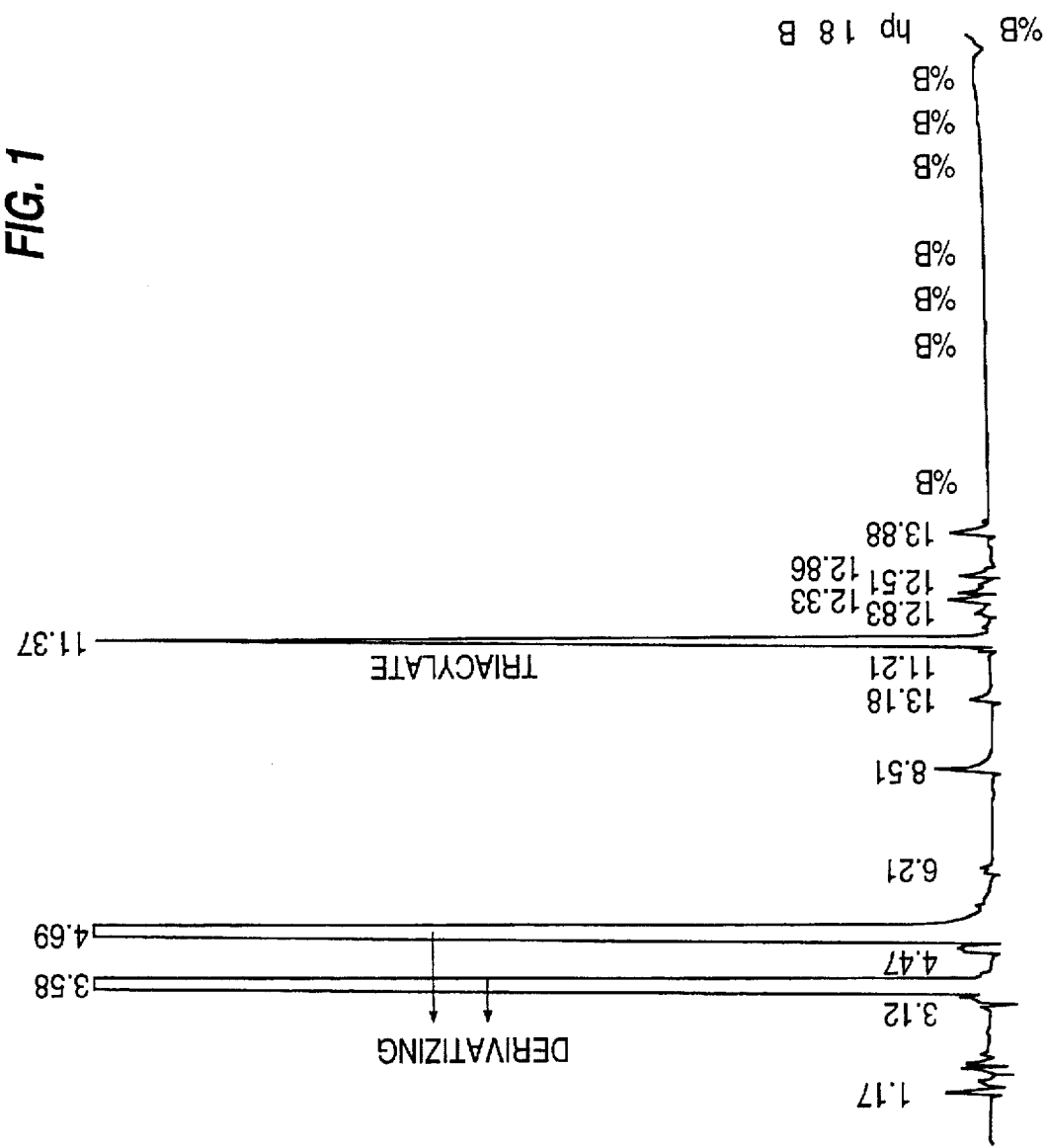

United States Patent [19]

Mangia

[11] Patent Number: 5,763,587
[45] Date of Patent: Jun. 9, 1998

[54] PROCESS FOR THE SYNTHESIS OF AMIKACIN

[75] Inventor: Alberto Mangia, Milan, Italy

[73] Assignee: Gist Brocades Italy Spa, Italy

[21] Appl. No.: 834,991

[22] Filed: Feb. 14, 1992

Related U.S. Application Data

[63] Continuation of Ser. No. 637,932, Jan. 8, 1991, abandoned, which is a continuation of Ser. No. 276,855, Nov. 28, 1988, abandoned.

[30] Foreign Application Priority Data

Nov. 27, 1987 [IT] Italy ................. 22783A/87

[51] Int. Cl.$^6$ ................................. C07H 1/00
[52] U.S. Cl. .............. 536/13.8; 536/13.7; 536/18.5
[58] Field of Search ................. 536/13.7, 13.8, 536/18.5

[56] References Cited

U.S. PATENT DOCUMENTS

| | | | |
|---|---|---|---|
| 4,136,254 | 1/1979 | Nagabhushan et al. | 536/13.8 |
| 4,504,472 | 3/1985 | Takaya et al. | 574/36 |
| 4,547,492 | 10/1985 | Umezawa et al. | 536/13.7 |

OTHER PUBLICATIONS

Wright et al, Journal of Antibiotics, Jul. 1976 pp. 714–719.

*Primary Examiner*—Elli Peselev
*Attorney, Agent, or Firm*—Wenderoth, Lind & Ponack

[57] ABSTRACT

In the synthesis of amikacin, having the formula:

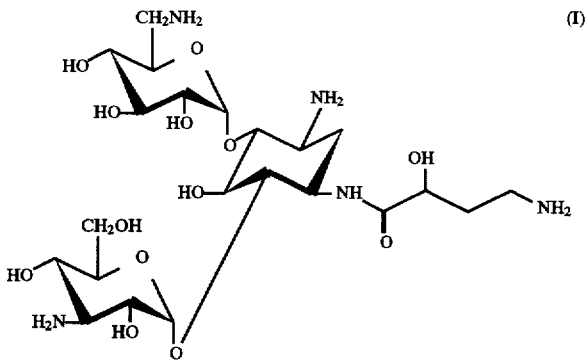

by acylation of a diprotected derivative of kanamycin A with a reactive derivative of L-(–)-4-amino-2-hydroxybutyric acid, the selection of the reaction solvent and of the pH conditions permit the industrial economically and the synthesis yield to be improved.

5 Claims, 2 Drawing Sheets

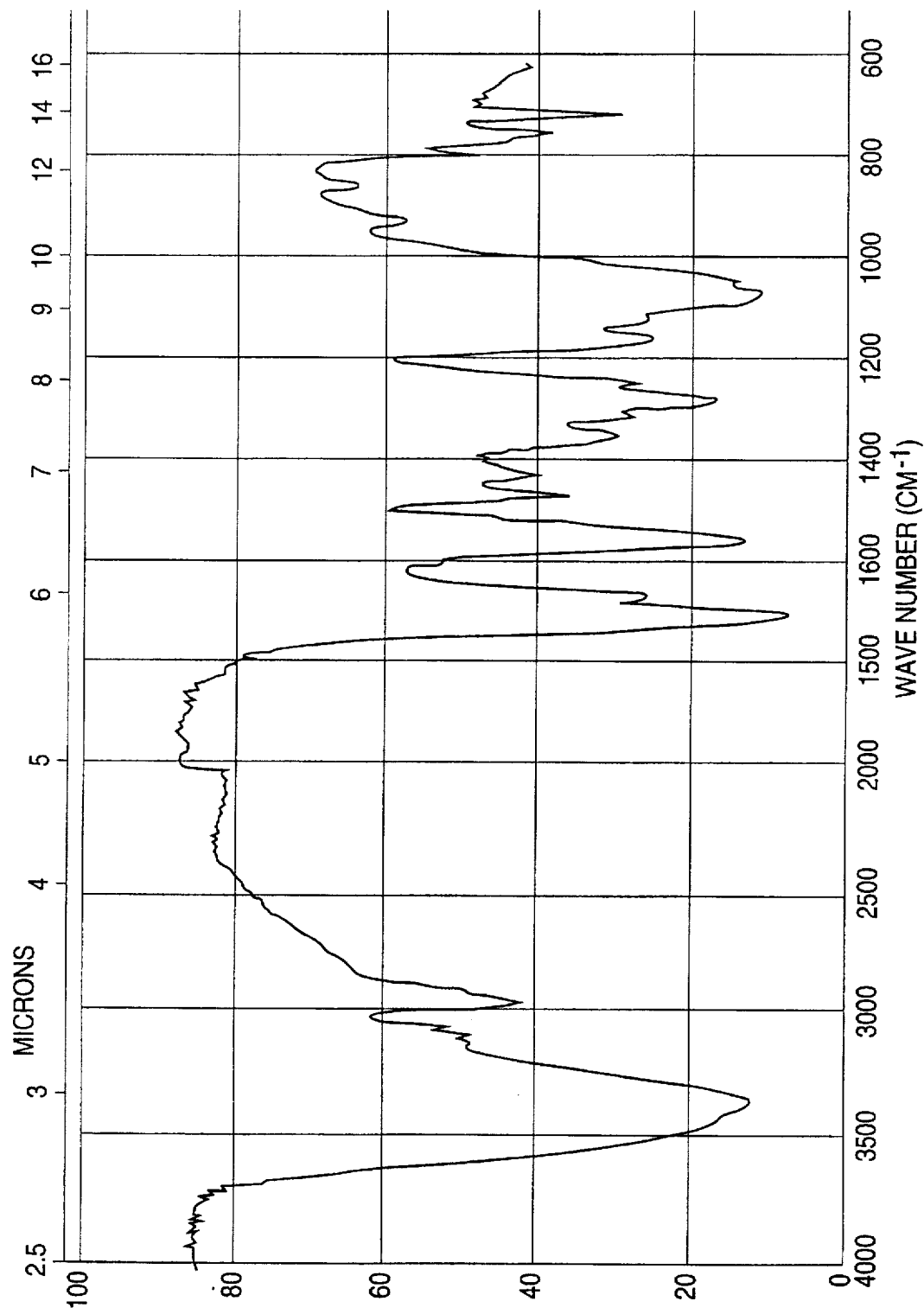

PROCESS FOR THE SYNTHESIS OF AMIKACIN

This application is a continuation of now abandoned application Ser. No. 07/637,932 filed on Jan. 8, 1991, now abandoned, which is a Continuation of now abandoned Ser. No. 07/276,855 filed Nov. 28, 1988, now abandoned.

Amikacin, (O-3-amino-3-desoxy-alpha-D-glucopyranosyl-(1→6)-O-[6--amino-6-desoxy-alpha-D-glucopyranosyl-(1→)]-$N^1$-(4-amino-2-hydroxy-1-oxybutyl)-2-desoxy-D-streptamine) of formula (I):

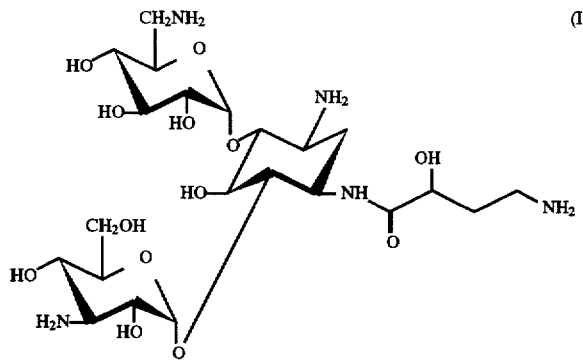

is a semisynthetic antibiotic, widely used in therapy, which formally derives from the acylation of kanamycin A (II)

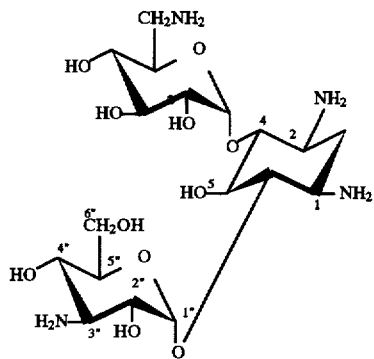

A number of synthesis schemes for amikacin are known and have been cited together with the corresponding literature in the European Patent Application No. 86.201.663.1 filed on Sep. 25, 1986 of the same Applicant.

The purpose of this invention is the selective acylation of the amino group in the position 1 of the 2-deoxy streptamine nucleus of a suitable derivative of kanamycin in the simplest possible way, avoiding the use of toxic, expensive and difficultly disposable solvents and reactants. The acylating agent is a derivative of the L-(−)-4-amino-2-hydroxy-butyric acid (III) (hereinafter called L-HABA) suitably activated and protected according to methods known in the literature:

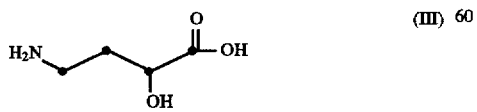

More particularly, the process of the present invention starts from the derivative (IV) protected in the positions N-6' and N-3 with the benzyloxycarbonyl group

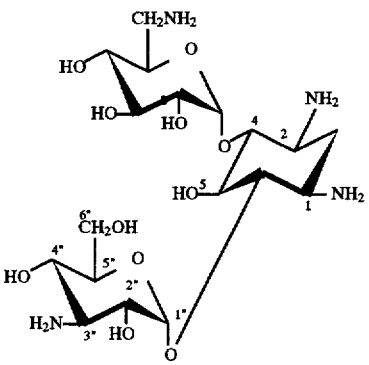

(IV): R=Ph—CH$_2$—OCO R'=H R"=H
(V): R=Ph—CH$_2$—OCO R'=CF$_3$CO R"=H
(VI): R=Ph—CH$_2$—OCO R'=H R"=CO—CH(OH)—CH$_2$—CH$_2$NH—CO—OCH$_2$Ø

Such an intermediate has been described by T. L. Nagabhushan et al., J. Amer. Chem. Soc., 100, 5254 (1978) and related U.S. Pat. No. 4,136,254 and in the papers of T. Tsuchiya et al., Tet. Lett., 4951 (1979) as well as in the Belgian Patent No. 879,925.

In the latter patent the diprotected intermediate (IV) is converted into the corresponding 3"-trifluoroacetamido compound (V) with ethyl trifluoroacetate and subsequently acylated in position 1 with the suitably selected L-HABA derivative.

The two different protecting groups, trifluoacetyl and benzyloxycarbonyl, are removed in this order by ammonia and hydrogen giving, as the final product, amikacin.

The yields are described as being satisfactory, but the process is not industrially convenient since ethyltrifluoacetate, a toxic and expensive reactant, and dimethyl sulfoxide , an expensive and difficultly recoverable solvent owing to its high boiling point, are to be used.

Also the possible disposal involves relevant additional costs.

The main purpose of the present invention is that of providing a process such that the problems and drawbacks as above shortly mentioned are solved.

The process of the present invention is characterized in that the acylation of the diprotected intermediate (IV) is carried out by using, as the solvent, exclusively water with the evident advantages for the industrial process both from the economical point of view and from the ecological one.

A second basic feature consists in that the intermediate (IV) is directly acylated to give the triacylated intermediate (VI) by controlling the reaction pH which is mainly responsible for the acylation selectivity between the amino groups in the positions 1 and 3".

Such an acylation selectivity is an original and novel result which was not foreseable on the basis of what is reported in the literature.

As a matter of fact the paper of J. J. Wright et al., J. Antibiotics, 29, 714 (1976) discusses the possibility that the selectivity of the reaction medium depends on the pH and that it is dramatically changed by selecting reaction conditions in which the amino groups of the antibiotic compound are fully protonated.

As a matter of fact, according to the information given by the authors, N-acylated derivatives of several aminoglucosides (sisomicyne, verdamycine, gentamycine $C_1a$) can be obtained with yields which are always lower than 30%.

In the same paper it is however clearly stated that "poor selectivity has been observed in the acylation of highly hydroxylated antibiotics such as gentamycin B and kanamycin".

On the basis of such an explicit statement, the fact that in the process of the present invention the acylation in the position of N-1 of a diacylated derivative of kanamycine is highly selective as a function of the reaction pH is fully novel and unforeseeable.

In the U.S. Pat. No. 4,136,254 of some of the above mentioned authors, in the example 23 a direct acylation of the same intermediate (IV) is mentioned in a homogeneous solution (50% V/V) of tetrahydrofuran and water with the active ester with N-hydroxy succinimide of the N-benzyloxycarbonyl L-HABA acid dissolved in DMF. However the operating conditions are different from those used in the present invention since the reaction, in the U.S. Patent, is carried out in homogeneous phase with complete solubilization of the reactants, whereas in the present method the reaction is carried out in heterogeneous phase (it being meant as heterogeneous phase the presence of a mixture of immiscible solvents or of a mixture of immiscible solvents and of a third solid phase) without the use of expensive solvents such as tetrahydrofuran and dimethylformamide. More particularly, the process of the present invention, starting from a kanamycin A protected in the positions 6'- and 3'-, comprises the reaction thereof with a suitably selected reactive derivative of L-HABA acid in a heterogeneous medium and under controlled pH.

The reaction product (VI) is then deprotected according to standard methods and the resulting raw product is purified by chromatography leading to amikacin with optimum yields.

More particularly, as the starting product, any derivative of kanamycin A can be used in which the amino groups in the positions 6- and 3- are protected by substitution of a hydrogen atom with an acyl group such as, for example, a benzyloxycarbonyl group or a substituted benzyloxycarbonyl group as p-nitrobenzyloxy carbonyl or p-methoxy benzyloxy carbonyl , an alkoxy carbonyl group, such as t-butoxy carbonyl or t-amyloxy carbonyl, the phthaloyl group, an halo alkyl carbonyl group such as trifluoroacetyl or chloroacetyl, or other suitable protecting groups. Preferably, anyhow, the amino groups in the positions 6' and 3 shall be protected with benzyloxy carbonyl or substituted benzyloxy carbonyl groups since, as already pointed out, these groups can be readily removed at the end of the reaction by catalytic reduction.

The starting products of this type can be prepared according to the method described in the Belgian Patent No. 855,704 or according to the method described in Canadian Patent No. 1,131,628.

Such a protected intermediate is then suspended in water at a predetermined pH which can vary from 3 to 10, the best results being obtained between 4.5 and 6.5 and is selectively acylated in the position 1 by adding the selected reactive derivative of L-HABA acid dissolved in an aprotic and poorly water soluble solvent.

Among the organic solvents which can be suitably used there are the aliphatic hydrocarbons and the halogenated compounds such as methylene chloride, chloroform, 1,2-dichloroethane, etc.

The reaction is carried out at a temperature of between 0° C. and 60° C. for some hours under stirring.

Once the reaction is completed, the organic solvent is evaporated and protecting groups in the positions 3 and 6' are removed according to conventional methods.

For example when, according to a preferred feature of the invention, the protecting groups are carbobenzyloxy carbonyl groups, possibly substituted, they are removed by standard catalytic hydrogenolysis with a platinum, palladium, palladium oxide or platinum oxide catalyst and, when these protecting groups are phtaloyl groups, the latter are readily removed by hydrolysis with hydrazine, or even t-butoxy carbonyl protecting groups are conveniently removed with formic acid etc.

The thus obtained raw product is then purified by chromatographic techniques known in the literature for the purification of amikacin.

The acylation carried out according to the process of the present invention on the 3,6'-di-N-protected kanamicin A under conditions of controlled pH and in heterogeneous phase gives places to a regio-selectivity which is unexpectedly very high since preferably amikacin is formed instead of BB-K11 or of the products deriving from the double acylation at N-1 and N-3". It is, moreover, very relevant that according to the present method, in the final product there can be present, as possibly potential impurities, only the product called BB-K11 and the product diacylated at N-1 and N-3" positions, the toxicity of which is lower than than of the product called BB-K29, which is the main potential impurity which is formed according to the other known synthetic methods.

The process of the present invention, which shows high characteristics of yield and purity of the product, is particularly safe from the point of view of industrial hygienics since almost harmless reactants and solvents are used and the process is readily carried out since no intermediate must be separated.

As regards the reaction product (VI) coming from the selective acylation according to the process of the invention, the chemical and physical properties thereof have never been described beforehand, although it is a reaction product cited in the U.S. Pat. No. 4,136,254 and non separated intermediate mentioned in the already cited Tsuchiya paper.

Instead of directly carrying out the removal of the three protecting groups present on the amino groups of the intermediate (VI), this intermediate can be precipitated in order to improve the purification level and then the synthesis is subsequently performed with lower amounts of by-products.

The analytical determinations carried out for this intermediate of basic importance for the process of the invention gave the following results Total nitrogen according to Kjeldahl: 7.16% (theoretical 7.09—molecular weight 988.03).

potentiometric titre with 0.1N $HClO_4$: 96% of the theoretical;

free acidity (expressed as formic acid) : 0.5% free ammonia: absent.

Further chromatographic determinations both by thin layer (TLC) and by liquid chromatograpy (HPLC) have been carried out on this intermediate (VI).

The TLC conditions were the following:

Merck silica gel plates for analytical chromatography, eluant: a mixture comprising 125 parts (by volume) of chloroform, 60 parts of methanol, 5 parts of acetic acid and 10 parts of $H_2O$ The chromatographic chamber is pre-saturated and after the run it is dried in hot air stream.

The visive detection is carried out with a solution of hydrochloric acid in ethanol, (10% v/v), the chamber is dried again in a hot air stream and is sprayed with ninidrin. Lastly it is maintained for five minutes in oven at 105° C.

The spots relating to the potential by products, which are tetracylates of kanamicin (with the four amino groups blocked by the selected protecting group) and triacylates of kanamicin (in which the third protecting group is substituted at N-1 or N-3', besides the two groups at N-3 and N-6') are normally less than 2% according to the comparison with the standard sample.

As regards the HPLC analysis, it is carried out under the following conditions:

column: RB-8.5 μm; 250 mm×4.6 mm (Brownlee Labs)
eluant: A) Buffer solution $KH_2PO_4$ at 2.5 (1.36 g of $KH_2PO_4$ dissolved in 1 liter of water, brought to the desired pH with 5% phosphoric acid, filtered on filter at 0.45 μm).
B) mixture of acetonitrile -buffer at pH 2.5 (80/20 v/v), flow rate 2 ml/minute.
gradient: from 15% B to 90% B in 15 minutes.
temperature: 30° C.
detection: UV/350 nm derivatizing solution: 2,4,6-trinitrobenzensulfonic acid in water-pyridine (50/50).

In the enclosed figures, FIG. 1 shows an HPLC pattern, whereas FIG. 2 shows the IR spectrum in $KB_r$.

According to this synthesis scheme, moreover, the isomeric product of amikacin, called BB K29, which is more toxic than amikacin, can not be formed.

The potentially present impurities can be only BB-K11 and the product deriving from the double acylation at N-1 and N-3".

Some experiments have been thus carried out for the comparison of the death rate, toxicity and acute general tolerability, between the product available in the market from Bristol Myers (BB-K8), amikacin produced according to the synthesis of the present invention and the potential impurities (BB K11, BB K29 and the diacylate with L-HABA at N-1 and N-3"), in mice by intravenous administration (caudal vein) to groups of 10 animals. The $LD_{50}$ values have been calculated by the Finney-Probits method.

The results are the following:

|  | $LD_{50}$ (mg/kg) | 5% reliability limits |
|---|---|---|
| BB-K8 Bristol | 202.3 | (170–228) |
| Amikacin | 241 | (241–271) |
| BB-K29 | 126 | (119–134) |
| BB-K11 | 356 | (264–480) |
| Diacylate (N-1 and N-3") | 268 | (247–290) |

The above data show without doubt the superiority of the present synthesis method since final products are obtained in which the possible impurities, although present in very low amounts in the final products, are anyhow much less toxic than BB-K29 which can be present in syntheses different from that of the present invention.

In order to better illustrate the process of the invention some examples are reported hereinafter, which are not to be meant as a limitation.

EXAMPLE 1

53.4 g of intermediate (IV) are suspended in 1000 ml of water and dissolved with 38.5 ml of acetic acid; after 30 minutes stirring at room temperature , the pH is adjusted with 30% NaOH up to 6 (about 52 ml).

After further 30 minutes at room temperature, 34.9 g of N-benzyloxy-carbonyl-L-HABA-N-hydroxy succinimide dissolved in 1442 ml of methylene chloride are added in one time.

The mixture is then maintained under vigorous stirring at room temperature for one night, then the organic solvent is evaporated at temperature lower than 40° C. and the pH is adjusted with acetic acid up to a value of 4.2.

The deprotection of the three benzyloxycarbonyl protecting groups is carried out with a standard method, by adding to the solution 50 g of 2.5% of Pd/C and by adding dropwise at room temperature 50 ml of formic acid. After filtration of the carbon on decalite and water washing, there are obtained 1900 ml of rich waters , having the following compositions:

| amikacin | 11,52 g/l |
|---|---|
| kanamycin A | 2 g/l |
| BBK 11 | 0.25 g/l |
| di (HABA) KANA | 1.3 g/l | corresponding to a stoichiometrical yield of amikacin of 65% starting from the diacylate (IV).

This solution is absorbed on a ionic exchange resin, type Zerolit (Trade Mark of ROHM and HAAS), in the weakly acid form, after adjustment of pH to 7.5.

The kanamycin is eluted with a linear gradient of ammonia from 0.5N to 1.5N, and comes out by first from the column followed by the amikacin. The fractions 300–350 are collected and concentrated under vacuum for the total elimination of all the ammonia and to achieve a final concentration of amikacin of 20%.

50% p/v $H_2SO_4$ is used to acidify at ph 2.5 and a treatment with carbon is carried out.

After 30 minutes stirring at room temperature, the carbon is filtered, the residue is washed and amikacin disulfate is precipitated with methanol.

After 2 h stirring at room temperature, the obtained white solid is filtered and after washing and drying under vacuum at 45° C. for 16 h, has weight of 33.3 g.

The titre of amikacin base is 68% as determined by HPLC (with a microbiological title of 690/μg/mg) the other specifications are in accordance with those of amikacin sulfate.

EXAMPLE 2

50 g of 3,6'-di-N-benzyloxycarbonylkanamycin A (IV) having an HPLC assay of 89.5% (59.3 mmoles), a water content of 3.3% and having as the main impurity 1,3,6'-tri-N-benzyloxycarbonylkanamycin A, is suspended in 1500 ml of deionized water. After 30 minutes stirring, glacial acetic acid is added in the amount necessary to bring the pH value to 6±0.2.

At that point a solution is practically obtained. The active ester of N-hydroxysuccinimide of the L-(−)-gamma-benzyloxycarbonyl amino-alpha-hydroxybutyric acid is added at room temperature as a solution of methylene chloride (25 g corresponding to 80.6 mmoles) in 1000 ml of solvent.

The stirring of the mixture is maintained at high value for about 2 h and the mixture is maintained under stirring for the whole night.

After separation of the organic phase, it is brought to pH 10 by means of a 3N $NH_3$ solution.

The thus formed white precipitate is filtered on Buckner under vacuum and washed with water.

The slightly crystalline solid is dried under vacuum at 30° C. for about 30 hours.

There are obtained 30.9 g of 3,6'-di-N-benzyloxycarbonyl-1-N-L-(−)-gamma-benzyloxycarbonylamino-alpha-hydroxybutyryl-kanamycin A (VI) having a title of 70% (HPLC).

The main impurities are:

starting diacylate (IV)<1% triacylate (N-1, N-3 and N-6' with benzyloxycarbonyl groups ): 2% drying losses: 4.5% (3 hours , 105° C.).

sulfuric ashes: 0.15%.

I claim:

1. A process for the synthesis of amikacin having the formula:

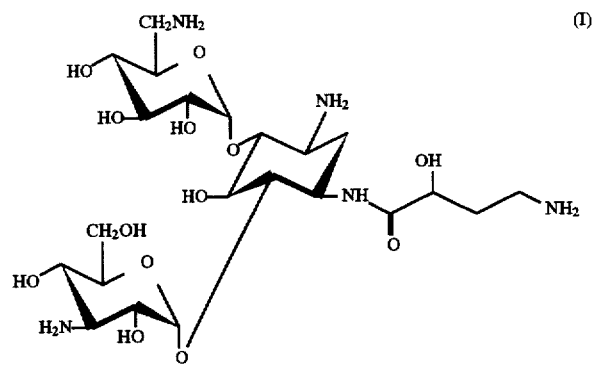

which consists essentially of acylating a diprotected derivative of kanamycin A, having the formula:

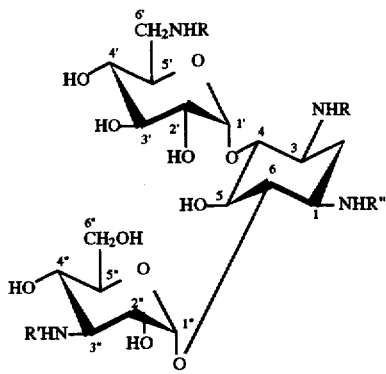

wherein R is an acyl protecting starting group selected from the group consisting of benzyloxycarbonyl, substituted benzyloxycarbonyl, alkoxycarbonyl, phthaloyl, and haloalkylcarbonyl and R' and R" are H, with N-benzyloxy L-(−)-4-amino-2- hydroxybutyric acid N-hydroxysuccinimide, the protecting starting groups being then removed from the reaction product, and said acylation being carried out in a reaction solvent consisting essentially of water and a solvent poorly soluble in water and by controlling the pH to a value of between 4.5 and 6.5, the reaction temperature being between 0° and 60° C.

2. The process according to claim 1, wherein said acyl protecting starting group is selected from the group consisting of benzyloxy-carbonyl, p-nitrobenzyloxycarbonyl and p-methoxybenzyloxy-carbonyl.

3. The process according to claim 1, wherein said aprotic solvent poorly soluble in water is selected from the group consisting of aliphatic hydrocarbons and halogenated aliphatic hydrocarbons.

4. The process according to claim 3, wherein said solvent poorly soluble in water is selected from the group consisting of methylene chloride, chloroform and 1,2-dichloroethane.

5. The process according to claim 1 wherein said N-benzyloxy L-(−)-4-amino-2- hydroxybutyric acid N-hydroxysuccinimide is dissolved in said solvent which is poorly soluble in water.

\* \* \* \* \*